United States Patent [19]

Fushimi et al.

[11] Patent Number: 5,599,981
[45] Date of Patent: Feb. 4, 1997

[54] PROCESS FOR PRODUCING ALKYLBENZOYL CHLORIDE

[75] Inventors: Norio Fushimi; Kenichi Nakamura; Makoto Takagawa, all of Tsukuba, Japan

[73] Assignee: Mitsubishi Gas Chemical Company, Inc., Tokyo, Japan

[21] Appl. No.: 590,598

[22] Filed: Jan. 24, 1996

[30] Foreign Application Priority Data

Jan. 26, 1995 [JP] Japan .................................. 7-010645
Jan. 26, 1995 [JP] Japan .................................. 7-010646

[51] Int. Cl.⁶ .................................................. C07C 51/58
[52] U.S. Cl. ........................................................ 562/863
[58] Field of Search .............................. 562/863

[56] References Cited

U.S. PATENT DOCUMENTS 3,274,242  9/1966  Etherington, Jr. et al. .
3,835,187  9/1974  Dyson .
3,894,923  7/1975  Grégoire .

FOREIGN PATENT DOCUMENTS 892879   5/1944   France .
1039053  3/1956   Germany .
1152637  11/1986  Japan .
2061257  5/1981   United Kingdom .

*Primary Examiner*—Paul J. Killos
*Attorney, Agent, or Firm*—Armstrong, Westerman, Hattori, McLeland & Naughton

[57] ABSTRACT

Provided is a process for producing alkylbenzoyl chloride which comprises reacting alkylbenzaldehyde with chlorine at a temperature of −10° to 80° C. under a pressure of 5 kg/cm² or below in a liquid phase, whereby alkylbenzoyl chloride can be produced in a high yield and at a low price.

7 Claims, No Drawings

PROCESS FOR PRODUCING ALKYLBENZOYL CHLORIDE

BACKGROUND OF THE INVENTION

1) Field of the Invention

The present invention relates to a process for producing alkylbenzoyl chloride by chlorination of alkylbenzaldehyde. Alkylbenzoyl chlorides have been widely used in various fields as starting materials or intermediates for agricultural chemicals, chemical synthetic products, etc.

2) Prior Art

Hitherto, as a process for producing benzoyl chlorides, it has been regarded that the process for producing benzoyl chlorides by hydrolysis of the corresponding benzotrichloride is economical.

On the other hand, a process which comprises chlorinating alkylbenzene carboxylic acid as a starting material with a chlorinating agent including thionyl chloride, phosphorus pentachloride, etc., thereby producing the corresponding acid chloride, a process for producing benzoyl chloride by the reaction of benzaldehyde having no alkyl side chain with chlorine (U.S. Pat. No. 3,894,923), etc., are known.

Among the processes, in the process for producing alkylbenzoyl chloride by hydrolysis of the corresponding alkylbenzotrichloride, alkylbenzotrichloride as a starting material is indispensable. In order to obtain alkylbenzotrichloride, only one methyl group on alkylbenzene having at least two alkyl-substituted groups need to be selectively chlorinated. Thus, it is very difficult to carry out selectively such reaction.

Moreover, in the process for chlorinating alkylbenzene carboxylic acid with thionyl chloride, etc., the yield of acid chloride is high, but the use the chlorinating agent is more expensive than that in case of chlorine being used as starting material and causes many problems in purification and post treatment.

On the other hand, in the process for producing benzoyl chloride by reacting benzaldehyde with chlorine, benzoyl chloride can be obtained in a high yield. Therefore, the process is very excellent as a process for producing benzoyl chloride having no alkyl-substituted group. However, in the reaction alkylbenzaldehyde having an alkyl side chain(s) as starting material with chlorine, it is difficult to obtain the corresponding alkylbenzoyl chloride in a high yield. No industrial process for producing alkylbenzoyl chloride is known because alkyl group as side chain in alkylbenzaldehyde readily reacts with chlorine. Thus, by the reaction of alkyl group with chlorine, side chain chloride of alkylbenzaldehyde as the starting material and side chain chloride of the intended alkylbenzoyl chloride, etc., are readily by-produced in a large amount and the yield of the intended alkylbenzoyl chloride often markedly deteriorates. Furthermore, since the boiling point of the intended alkylbenzoyl chloride is close to that of by-products, the separation by distillation is difficult, so that problems in purification occur.

SUMMARY OF THE INVENTION

An object of the present invention is to provide a process for producing alkylbenzoyl chloride from alkylbenzaldehyde and chlorine in a high yield and at a low price.

As a result of extensive studies for excellent process for producing alkylbenzoyl chloride, the present inventors have found that side reactions including chlorination for nucleus and chlorination for side chain, etc are suppressed and the intended alkylbenzoyl chloride can be obtained in a very high yield by reacting alkylbenzaldehyde with chlorine at a low temperature in a liquid phase, and have established the present invention.

That is, the present invention provides a process for producing alkylbenzoyl chloride which comprises reacting alkylbenzaldehyde with chlorine at a temperature of −10° to 80° C. under a pressure of 5 kg/cm$^2$ or below in a liquid phase.

In the chlorinating reaction according to the present invention, production of by-products including side chain chlorides, etc., are suppressed and high boiling point products decreases, whereby alkylbenzoyl chloride can be obtained in a further high yield, by carrying out the reaction in the presence of at least one compound selected from the group consisting of o-dichlorobenzene, chlorobenzene, carbon tetrachloride and benzonitrile, substituted benzene having at least one functional group selected from the group consisting of methyl group, chloromethyl group, dichloromethyl group and trichloromethyl group or a mixture of the above-mentioned compound and the substituted benzene.

DETAILED DESCRIPTION OF THE INVENTION

The present invention will be described in detail below.

Alkylbenzaldehyde being used as starting material in the present invention is a compound being represented by the chemical formula (I):

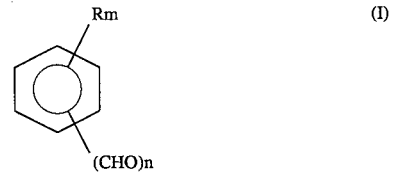

wherein R represents an alkyl group having 1 to 8 carbon atoms, and m and n are integers of 1 to 5 showing the number of substituted group, m+n≦6, or a mixture of compounds being represented by the same general formula (I) as defined above wherein R, m and n are the same as defined above and each R among the compounds is different from each other.

Examples of alkylbenzaldehyde include o-, m- and p-tolualdehyde, ethylbenzaldehyde, isopropylbenzaldehyde, isobutylbenzaldehyde, 2, 4-dimethylbenzaldehyde, 2, 6-dimethylbenzaldehyde, 2, 4, 5-trimethylbenzaldehyde etc., whereby the corresponding alkylbenzoyl chloride is obtained.

Regarding chlorine being used in the present invention, when industrially available chlorine is used, it will be not particularly limited. It is preferred to use dried chlorine. Usually, the reaction is carried out by bubbling the reaction solution with chlorine. In this case, feeding amount and feed rate of chlorine are not particularly limited.

The reaction pressure is 5 kg/cm$^2$ or below. Usually, the reaction is carried out under atmospheric pressure.

In the present invention, as described above, production of by-products including side chain chlorides, etc., is suppressed, whereby alkylbenzoyl chloride can be obtained in a further high yield, by carrying out the reaction in the presence of at least one compound selected from the group consisting of o-dichlorobenzene, chlorobenzene, carbon tetrachloride and benzonitrile, substituted benzene having at least one functional group selected from the group consisting of methyl group, chloromethyl group, dichloromethyl group and trichloromethyl group or a mixture of the above-mentioned compound and the substituted benzene.

The above-mentioned compound provides the advantageous effects even in a small amount thereof, and is used preferably in an amount of 0.5 to 100 parts by weight, more preferably in an amount of 1.0 to 50 parts by weight per 1 part by weight of alkylbenzaldehyde as starting material. When the amount being used is above 100 parts by weight, it is not economical since recycling amount of the above-mentioned compound increases, though it exerts no influence on the reaction efficiency.

The substituted benzene may further have substituted group including halogen group, nitrile group, etc,, and is represented by the general formula (II):

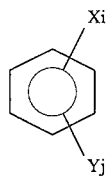
(II)

Wherein X represents one functional group selected from the group consisting of methyl group, chloromethyl group, dichloromethyl group and trichloromethyl group; Y represents one functional group including —F, —Cl, Br—, —I, —CN, —COCl, —NO$_2$, —C$_6$H$_5$, —C$_6$H$_5$CH$_3$, etc.,; i is an integer of 1 to 6 showing the number of substituted group X; j is an integer of 0 to 5 showing the number of substituted group Y; i+j≦6.

Examples of the substituted benzene include toluene, o-, m-and p-xylene, psuedocumene, mesitylene, benzyl chloride, benzal chloride, benzotrichloride, o-, m- and p-tolunitrile, 4-methylbiphenyl, 4,4'-dimethylbiphenyl, o-, m- and p-α, α, α, α', α', α'- hexachloroxylene, etc.

The substituted benzene is use preferably in an amount of 0.001 to 100 parts by weight, more preferably in an amount of 0.005 to 50 parts by weight per 1 part by weight of alkylbenzaldehyde as starting material. When the amount of the substituted benzene being used is above 100 parts by weight, it is not economical, though it exerts no influence on the reaction efficiency, whereas below 0.001 parts by weight it is unpreferable since by-products including nucleus chlorides, side chain chlorides, etc., and high boiling point products, etc., are produced, whereby the yield of intended acid chloride decreases.

In the process according to the present invention, production of by-products including side chain chlorides, etc., is suppressed, whereby alkylbenzoyl chloride can be obtained in a further high yield, by carrying out the reaction in the presence of a mixture of the above-mentioned compound and the substituted benzene.

The reaction in the present invention can be carried out in the absence of a catalyst. Usually, it is carried out under exposure. The light source is not particularly limited. Industrially, high reaction activity and high selectivity to acid chloride are obtained by placing mercury lamp, tungsten lamp, etc., as light source inside the reactor. Also use of a radical initiator such as benzoyl peroxide or 2,2-azobis(isobutylonitrile), etc., instead of exposure is effective in improving reaction activity. The radical initiator is used in a small amount thereof. The amount is satisfactory in an amount of about 0.001 to 0.01 parts by weight per 1 part by weight of alkylbenzaldehyde as starting material. When the amount of the radical initiator being used is above 0.01 parts by weight, it is economically unpreferable since no the yield is changed.

Control of the reaction temperature is very important in carrying out the process according to the present invention.

The reaction temperature is in the range of −10° to 80° C., preferably 0° to 50° C., more preferably 0° to 35° C.. When the reaction temperature is above 80° C., chlorination for alkyl side chain, chlorination for nucleus, side reactions including production of high boiling point components due to polymerization of the starting material with products, etc., readily occur, whereby the yield of the intended product markedly decreases, whereas below −10° C. the reaction activity not only deteriorates, but also in some cases the temperature of the starting material or products becomes lower than freezing point.

PREFERRED EMBODIMENT OF THE INVENTION

The present invention will be described in detail below, referring to Examples, which are not limitative.

EXAMPLE 1

70 g of p-ethylbenzaldehyde and 210 g of o-dichlorobenzene were charged into a flask having a capacity of 500 ml, provided with a gas blowing pipe, a reflux condenser and a stirrer and then the temperature of the interior was adjusted to 5° C. while introducing nitrogen from the gas blowing pipe. The reaction liquid was bubbled with nitrogen for one hour and then feeding of nitrogen was stopped. The reaction was started by beginning both feeding of chlorine and light irradiation with a mercury lamp. 38 g of chlorine was fed over one hour while maintaining the reaction temperature to 5° C. to carry out the reaction under atmospheric pressure.

The reaction product was analyzed by gaschromatography. As a result, the conversion of p-ethylbenzaldehyde was 90% and the selectivity to p-ethylbenzoyl chloride was 75%.

EXAMPLE 2

The reaction was carried out in the same manner as in Example 1 except that a flask having a capacity of 200 ml was used instead of a flask having a capacity of 500 ml and no o-dichlorobenzene was used.

As a result, the conversion of p-ethylbenzaldehyde was 87% and the selectivity to p-ethylbenzoyl chloride was 52%.

EXAMPLE 3

The reaction was carried out in the same manner as in Example 1 except that 70 g of p-tolualdehyde was used instead of 70 g of p-ethylbenzaldehyde and 42 g of chlorine was fed instead of 38 g of chlorine.

As a result, the conversion of p-tolualdehyde was 93% and the selectivity to p-toluoyl chloride was 80%.

EXAMPLE 4

The reaction was carried out in the same manner as in Example 1 except that 70 g of p-isopropylbenzaldehyde was used instead of 70 g of p-ethylbenzaldehyde and 33 g of chlorine was used instead of 38 g of chlorine.

As a result, the conversion of p-isopropylbenzaldehyde was 88% and the selectivity propylbenzoyl chloride was 73%.

EXAMPLE 5

The reaction was carried out in the same manner as in Example 1 except that 70 g of 2, 4-dimethylbenzaldehyde was used instead of 70 g of p-ethylbenzaldehyde.

As a result, the conversion of 2, 4-dimethylbenzaldehyde was 90% and the selectivity to 2, 4-dimethylbenzoyl chloride was 70%.

EXAMPLE 6

The reaction was carried out in the same manner as in Example 1 except that 30 g of p-ethylbenzaldehyde and 270 g of o-dichlorobenzene were charged instead of 70 g of p-ethylbenzaldehyde and 210 g of o-dichlorobenzene, and the reaction temperature of 30° C. were applied instead of the reaction temperature of 5° C. and 16 g of chlorine was used instead of 38 g of chlorine.

As a result, the conversion of p-ethylbenzaldehyde was 92% and the selectivity to p-ethylbenzoyl chloride was 80%.

EXAMPLE 7

The reaction was carried out in the same manner as in Example 1 except that 0.5 g of 2, 2-azobis(isobutylonitrile) was further added and no light irradiation with a mercury lamp was carried out.

As a result, the conversion of p-ethylbenzaldehyde was 85% and the selectivity to p-ethylbenzoyl chloride was 69%.

COMPARATIVE EXAMPLE 1

The reaction was carried out in the same manner as in Example 1 except that the reaction temperature of 150° C. was applied instead of the reaction temperature of 5° C.

As a result, the conversion of p-ethylbenzaldehyde was 95% and the selectivity to p-ethylbenzoyl chloride was 30%.

COMPARATIVE EXAMPLE 2

The reaction was carried out in the same manner as in Example 1 except that the reaction temperature of 130° C. was applied instead of reaction temperature of 5° C. and no o-dichlorobenzene was added.

As a result, the conversion of p-ethylbenzaldehyde was 97% and the selectivity to p-ethylbenzoyl chloride was 23%.

EXAMPLE 8

70 g of p-ethylbenzaldehyde, 20 g of toluene and 210 g of o-dichlorobenzene were charged into a flask having a capacity of 500 ml, provided with a gas blowing pipe, a reflux condenser and a stirrer and then the temperature of the interior was adjusted to 10° C. while introducing nitrogen from the gas blowing pipe. The reaction liquid was bubbled with nitrogen for one hour and then feeding of nitrogen was stopped. The reaction was started by beginning both feeding of chlorine and light irradiation with a mercury lamp. 38 g of chlorine was fed over one hour while maintaining the reaction temperature to 10° C. to carry out the reaction under atmospheric pressure.

The reaction produced liquid was analyzed by gaschromatography. As a result, the conversion of p-ethylbenzaldehyde was 92% and the selectivity to p-ethylbenzoyl chloride was 85%.

EXAMPLE 9

The reaction was carried out in the same manner as in Example 8 except that a flask having a capacity of 200 ml was used instead of a flask having a capacity of 500 ml and no o-dichlorobenzene was used.

As a result, the conversion of p-ethylbenzaldehyde was 87% and the selectivity of p-ethylbenzoyl chloride was 78%.

EXAMPLE 10

The reaction was carried out in the same manner as in Example 8 except that 10 g of benzyl chloride was used instead of 20 g of toluene.

As a result, the conversion of p-ethylbenzaldehyde was 93% and the selectivity to p-ethylbenzoyl chloride was 83%.

EXAMPLE 11

The reaction was carried out in the same manner as in Example 8 except that 4 g of benzotrichloride was used instead of 20 g of toluene.

As a result, the conversion of p-ethylbenzaldehyde was 95% and the selectivity to p-ethybenzoyl chloride was 86%.

EXAMPLE 12

The reaction was carried out in the same manner as in Example 8 except that 70 g of p-isopropylbenzaldehyde was used instead of 70 g of p-ethylbenzaldehyde and 33 g of chlorine was used instead of 38 g of chlorine.

As a result, the conversion of p-isopropylbenzaldehyde was 92% and the selectivity to p-isopropylbenzoyl chloride was 78%.

COMPARATIVE EXAMPLE 3

The reaction was carried out in the same manner as in Example 8 except that no toluene was used.

As a result, the conversion of p-ethylbenzaldehyde was 90% and the selectivity to p-ethylbenzoyl chloride was 75%.

COMPARATIVE EXAMPLE 4

The reaction was carried out in the same manner as in Example 8 except that the reaction temperature of 150° C. was applied instead of the reaction temperature of 10° C.

As a result, the conversion of p-ethylbenzaldehyde was 95% and the selectivity to p-ethylbenzoyl chloride was 52%.

COMPARATIVE EXAMPLE 5

The reaction was curried out in the same manner as in Example 8 except that the reaction temperature of 13° C. was applied instead of reaction temperature of 10° C. and no o-dichlorobenzene was added.

As a result, the conversion of p-ethylbenzaldehyde was 97% and the selectivity to p-ethylbenzoyl chloride was 38%.

According to the present invention, industrially useful alkylbenzoyl chloride can be produced from alkylbenzaldehyde and chlorine in a high reaction efficiency and at a low price by one-stage reaction.

What is claimed is:

1. A process for producing alkylbenzoyl chloride which comprises reacting alkylbenzaldehyde with chlorine at a temperature of −10° to 80° C. under a pressure of 5 kg/cm$^2$ or below in a liquid phase.

2. The process according to claim 1, wherein the alkylbenzaldehyde is a compound being represented by the following general formula (I) or:

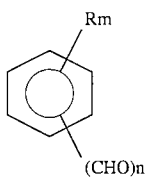

(I)

wherein R represents an alkyl group, and m and n are integers of 1 to 5 showing the number of substituted group, m+n≦6, or a mixture of compounds being represented by the same general formula (I) as defined above wherein R, m and n are the same as defined above and each R among the compounds is different from each other.

3. The process according to claim 1, wherein the reaction is carried out in the presence of at least one compound selected from the group consisting of o-dichlorobenzene chlorobenzene, carbon tetrachloride and benzonitrile.

4. The process according to claim 3, wherein the compound is used in an amount of 0.5 to 100 parts by weight per 1 part by weight of alkylbenzaldehyde.

5. The process according to claim 1, wherein the reaction is carried out in the presence of substituted benzene having at least one functional group selected from the group consisting of methyl group, chloromethyl group, dichloromethyl group and trichloromethyl group.

6. The process according to claim 5, wherein the substituted benzene is used in an amount of 0.001 to 100 parts by weight per 1 part by weight of alkyloenzaldehyde.

7. The process according to claim 1, wherein the reaction is carried out in the presence of both at least one compound selected from the group consisting of o-dichlorobenzene, chlorobenzene, carbon tetrachloride and benzonitrile and substituted benzene having at least one functional group selected from the group consisting of methyl group, chloromethyl group, dichloromethyl group and trichloromethyl group.

\* \* \* \* \*